United States Patent
Bottom (10) Patent No.: US 10,946,160 B2
(45) Date of Patent: Mar. 16, 2021

(54) MEDICAL VAPORIZER WITH CARRIER GAS CHARACTERIZATION, MEASUREMENT, AND/OR COMPENSATION

(71) Applicant: General Electric Company, Schenectady, NY (US)

(72) Inventor: Douglas Kirk Bottom, Watertown, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 333 days.

(21) Appl. No.: 15/467,483

(22) Filed: Mar. 23, 2017

(65) Prior Publication Data

US 2018/0272098 A1 Sep. 27, 2018

(51) Int. Cl.
*A61M 16/10* (2006.01)
*A61M 16/20* (2006.01)
(Continued)

(52) U.S. Cl.
CPC ...... *A61M 16/1005* (2014.02); *A61M 16/024* (2017.08); *A61M 16/0891* (2014.02); *A61M 16/104* (2013.01); *A61M 16/18* (2013.01); *A61M 16/201* (2014.02); *A61M 16/203* (2014.02); *G01N 29/024* (2013.01); *G01N 29/30* (2013.01); *G01N 33/0006* (2013.01);
(Continued)

(58) Field of Classification Search
CPC .......... A61M 16/1005; A61M 16/0891; A61M 16/201; A61M 16/104; A61M 16/12; A61M 2016/102; A61M 2205/502; G05D 11/131; G05D 11/135; G01N 29/024
See application file for complete search history.

(56) References Cited

U.S. PATENT DOCUMENTS

| 4,492,120 A | 1/1985 | Lewis et al. |
| 4,611,590 A | 9/1986 | Ryschka et al. |

(Continued)

FOREIGN PATENT DOCUMENTS

| EP | 0874238 | 10/1998 |
| EP | 0894506 | 2/1999 |

(Continued)

OTHER PUBLICATIONS

Proper Calibration of Gas Analyzers; Issue 11, vol. 114; published Nov. 1, 2010; retrieved Feb. 18, 2020; https://www.power-eng.com/2010/11/01/proper-calibration-of-gas-analyzers/#gref (Year: 2010).*

(Continued)

*Primary Examiner* — Bradley J Osinski
(74) *Attorney, Agent, or Firm* — Fletcher Yoder, P.C.

(57) ABSTRACT

A medical vaporizer is provided. In one embodiment, dual-purpose sensors are employed, such as in a configuration in which one is positioned in the mixed gas flow channel and one is positioned in the main gas flow channel. The sensors provide measurements that may be used to determine both gas flow and gas concentration in the mixed and main gas channels, even when the identity and/or properties of the gas in the main gas channel are unknown. The measurements derived from the dual-purpose sensors may be used to measure and report the total anesthetic being delivered at the vaporizer output and/or improve vaporizer accuracy.

10 Claims, 4 Drawing Sheets

(51) Int. Cl.
*A61M 16/00* (2006.01)
*A61M 16/18* (2006.01)
*G05D 21/02* (2006.01)
*A61M 16/08* (2006.01)
*G01N 29/024* (2006.01)
*G01N 29/30* (2006.01)
*G01N 33/00* (2006.01)
*G05D 11/13* (2006.01)
*A61M 16/22* (2006.01)
*A61M 16/12* (2006.01)

(52) U.S. Cl.
CPC ......... *G05D 11/131* (2013.01); *G05D 11/135* (2013.01); *G05D 21/02* (2013.01); *A61M 16/0075* (2013.01); *A61M 16/085* (2014.02); *A61M 16/0833* (2014.02); *A61M 16/12* (2013.01); *A61M 16/208* (2013.01); *A61M 16/22* (2013.01); *A61M 2016/0027* (2013.01); *A61M 2016/102* (2013.01); *A61M 2016/1035* (2013.01); *A61M 2202/025* (2013.01); *A61M 2202/0208* (2013.01); *A61M 2202/0225* (2013.01); *A61M 2202/0283* (2013.01); *A61M 2205/3334* (2013.01); *A61M 2205/3368* (2013.01); *A61M 2205/3375* (2013.01); *A61M 2205/502* (2013.01); *A61M 2205/60* (2013.01); *A61M 2205/70* (2013.01); *G01N 2291/021* (2013.01)

(56) References Cited

U.S. PATENT DOCUMENTS

| | | | |
|---|---|---|---|
| 5,060,506 | A | 10/1991 | Douglas |
| 5,060,514 | A | 10/1991 | Aylsworth |
| 5,247,826 | A | 9/1993 | Frola et al. |
| 5,369,979 | A | 12/1994 | Aylsworth et al. |
| 5,470,511 | A | 11/1995 | Laybourne et al. |
| 5,546,931 | A | 8/1996 | Rusz |
| 5,581,014 | A | 12/1996 | Douglas |
| 5,644,070 | A | 7/1997 | Gibboney et al. |
| 5,645,071 | A | 7/1997 | Harnoncourt et al. |
| 5,694,924 | A | 12/1997 | Cewers |
| 5,957,129 | A | 9/1999 | Tham et al. |
| 5,967,141 | A | 10/1999 | Heinonen |
| 6,050,283 | A | 4/2000 | Hoffman et al. |
| 6,116,235 | A | 9/2000 | Walters et al. |
| 6,131,571 | A | 10/2000 | Lampotang et al. |
| 6,155,255 | A | 12/2000 | Lambert |
| 6,275,650 | B1 | 8/2001 | Lambert |
| 6,279,378 | B1 | 8/2001 | Sheen et al. |
| 6,286,360 | B1 * | 9/2001 | Drzewiecki ........... A61B 5/083 702/24 |
| 6,443,150 | B1 | 9/2002 | Pessala et al. |
| 6,488,028 | B1 | 12/2002 | Lambert |
| 6,506,608 | B2 | 1/2003 | Mault |
| 6,634,239 | B2 | 10/2003 | Gomm et al. |
| 6,745,771 | B2 | 6/2004 | Castor et al. |
| 6,799,883 | B1 | 10/2004 | Urquhart et al. |
| 7,063,668 | B2 | 6/2006 | Cardelius et al. |
| 7,144,552 | B1 | 12/2006 | Fukuizumi et al. |
| 7,434,580 | B2 | 10/2008 | Downie et al. |
| 7,490,607 | B2 | 2/2009 | Bottom et al. |
| 7,810,988 | B2 | 10/2010 | Kamimura et al. |
| 7,886,783 | B2 | 2/2011 | Rindy et al. |
| 7,889,345 | B2 | 2/2011 | Shang et al. |
| 8,361,231 | B2 | 1/2013 | Kouketsu et al. |
| 8,365,724 | B2 * | 2/2013 | Bottom ............... A61M 16/104 128/203.14 |
| 8,752,544 | B2 | 6/2014 | Bottom |
| 8,752,548 | B2 | 6/2014 | Larsson et al. |
| 8,794,237 | B2 | 8/2014 | Wilkinson et al. |
| 9,289,569 | B2 | 3/2016 | Cardelius et al. |
| 2004/0093957 | A1 | 5/2004 | Buess et al. |
| 2004/0149285 | A1 | 8/2004 | Wallen |
| 2006/0096760 | A1 | 5/2006 | Ohmer |
| 2007/0107879 | A1 | 5/2007 | Radomski et al. |
| 2009/0090472 | A1 | 4/2009 | Radomski |
| 2010/0101571 | A1 * | 4/2010 | Messerges ........... A61M 16/104 128/203.14 |
| 2010/0224264 | A1 | 9/2010 | Homan et al. |
| 2010/0269821 | A1 | 10/2010 | Larsson et al. |
| 2012/0180724 | A1 | 7/2012 | Kouketsu et al. |
| 2015/0059745 | A1 | 3/2015 | Barker |
| 2017/0101715 | A1 | 4/2017 | Nishizato et al. |
| 2018/0272099 | A1 | 9/2018 | Bottom |

FOREIGN PATENT DOCUMENTS

| | | |
|---|---|---|
| EP | 0965372 | 12/1999 |
| GB | 415048 | 8/1934 |
| GB | 2029572 | 3/1980 |
| GB | 2255912 | 11/1992 |
| WO | WO9820926 | 5/1998 |
| WO | WO2004087244 | 10/2004 |
| WO | WO2004091708 | 10/2004 |
| WO | WO2008145177 | 12/2008 |

OTHER PUBLICATIONS

International Search Report and Written Opinion issued in connection with corresponding PCT Application No. PCT/US2018/023716 dated Jul. 9, 2018.
CA patent application 3,057,644 filed Sep. 23, 2049—Office Action dated Dec. 29, 2020; 7 pages.

* cited by examiner

MEDICAL VAPORIZER WITH CARRIER GAS CHARACTERIZATION, MEASUREMENT, AND/OR COMPENSATION

BACKGROUND

The subject matter disclosed herein relates generally to output accuracy of a medical vaporizer, such as may be part of an anesthesia machine.

Respiratory gas monitors may be employed to automatically measure and report levels of nitrous oxide and anesthetic agent present in breathing gases in a patient breathing circuit. As both of these gases contribute to the total amount of anesthetic given to the patient, it is useful for the clinician to know the levels of each. However, for various reasons, such as cost and variations in regulatory regimes, a respiratory gas monitor may not always be available at a given location. In such cases, the clinician must instead manually bring together separate information from the gas mixer and vaporizer and/or perform a calculation to determine the total amount of anesthetic being administered to the patient.

Thus, in situations where no respiratory gas monitor is employed while practicing anesthesia, there may be situations where the total anesthetic being administered to the patient may not fully account for the nitrous oxide present due to the inconvenience of gathering information and/or performing a calculation. Thus, there is a need for having improved accuracy with respect to vaporizer output in an anesthetic context. In particular, there is a need for improved reporting accuracy with respect to all agents having an anesthetic effect so a clinician can readily assess total potential anesthetic effect.

BRIEF DESCRIPTION

In one embodiment, a medical vaporizer is provided. In accordance with this embodiment, the medical vaporizer includes: a main gas channel through which a first flow of a first gas flows during operation; a side gas channel comprising one or more side channel control valves that during operation control a second flow of a second gas through the side gas channel; a mixed gas channel configured to receive the first flow of the first gas and the second flow of the second gas during operation and to output a mixed gas; a first dual-purpose sensor positioned in the main gas channel and configured to generate a first set of measurements during operation; a second dual-purpose sensor positioned in the mixed gas channel and configured to generate a second set of measurements during operation; and a vaporizer controller configured to receive the first set of measurements and the second set of measurements, to calculate, one or more of the identity of one or more components (i.e., constituents) of the first gas or concentration of one or more components of the first gas, to calculate, concentration of one or more components of the mixed gas, and to control operation of one or more of the side channel control valves based upon one or more of the calculated identities or concentrations. In one implementation, a display may be provided to display to a user one or more of the identity of one or more components of the first gas, concentration of one or more components of the first gas, or concentration of one or more components of the mixed gas.

In a further embodiment, a method for operating a medical vaporizer is provided. In accordance with this embodiment, a first ultrasonic sensor positioned in a main gas channel of the medical vaporizer is exposed to a first gas and one or more first measurement sets are acquired from the first ultrasonic sensor for the first gas. A stored calibration measurement set is accessed. One or more of the identity of one or more components of the first gas or concentration of one or more components of the first gas are calculated using the one or more first measurement sets and the stored calibration measurement set. The identity of one or more components of the first gas or concentration of one or more components of the first gas may be displayed to a user in one implementation.

In an additional embodiment, a method for operating a medical vaporizer is provided. In accordance with this embodiment, a first gas is flowed through a main gas channel. A second gas is flowed through a side gas channel. The first gas and second gas are combined to form a mixed gas in a mixed gas channel. A first set of measurements is generated using a first ultrasonic sensor positioned in a main gas channel and a second set of measurements is generated using a second ultrasonic sensor positioned in a mixed gas channel. One or more of the identity of one or more components of the first gas or concentration of one or more components of the first gas are calculated using one or more first measurement sets. One or more of, one or more main gas channel flow correction factors, one or more mixed gas channel flow correction factors, or one or more mixed gas concentration correction factors are calculated using one or more of the identity of one or more of the components of the first gas or concentration of one or more of the components of the first gas. One or more corrected flows or corrected concentrations are calculated using one or more of the main gas channel flow correction factors, the mixed gas channel flow correction factors, or the mixed gas channel concentration correction factors. The one or more corrected concentrations may be displayed to a user in one implementation.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present approach employs two dual-purpose sensors. In one embodiment, each sensor includes a gas conduit upon which at least a pair of ultrasonic transducers are positioned such that sound traveling between the transducers is influenced by the gas flow and composition in the conduit. The ultrasonic transducers, in such an embodiment, may be operated by one of (or a combination of) software executed on a suitable microprocessor and/or an application specific integrated circuit (ASIC). Such electrical components may be located within or proximate the sensor or remote from, but in communication with, the sensor, such as in a controller or control interface. By way of example such electronics and/or software may, when in operation, generate electrical signals to excite the transducers and/or receive or readout corresponding or responsive electrical signals generated by the transducers. The signals acquired from the transducers may be processed into a measurement set for use in accordance with the approach discussed herein.

The measurement set can include an upstream time-of-flight, a downstream time-of-flight, and/or an across time-of-flight (which is not affected by flow). These time-of-flight measurements can be used in the calculation of one or more of a flow, identity, or concentration of the gas or one or more of its components in the conduit. The identity and/or concentration of a component of the gas in the main channel may be calculated using at least one of the time-of-flight measurements from the sensor in the main channel. The concentration of one or more components of the gas in the mixed gas channel may be calculated using at least one of the time-of-flight measurements from each sensor.

Thus, in accordance with this approach, input carrier gas identity and/or properties can be determined by the medical vaporizer itself and can provide the basis for reporting clinically relevant information to a clinician and/or for compensating vaporizer operation to be virtually independent of input carrier gas. The former enables a convenient measurement of total anesthetic being administered, such as when nitrous oxide is present in the input carrier gas. The latter enables more accurate output control and/or reporting of measured parameters when the input carrier gas identity and/or properties are unknown.

Figure 1:
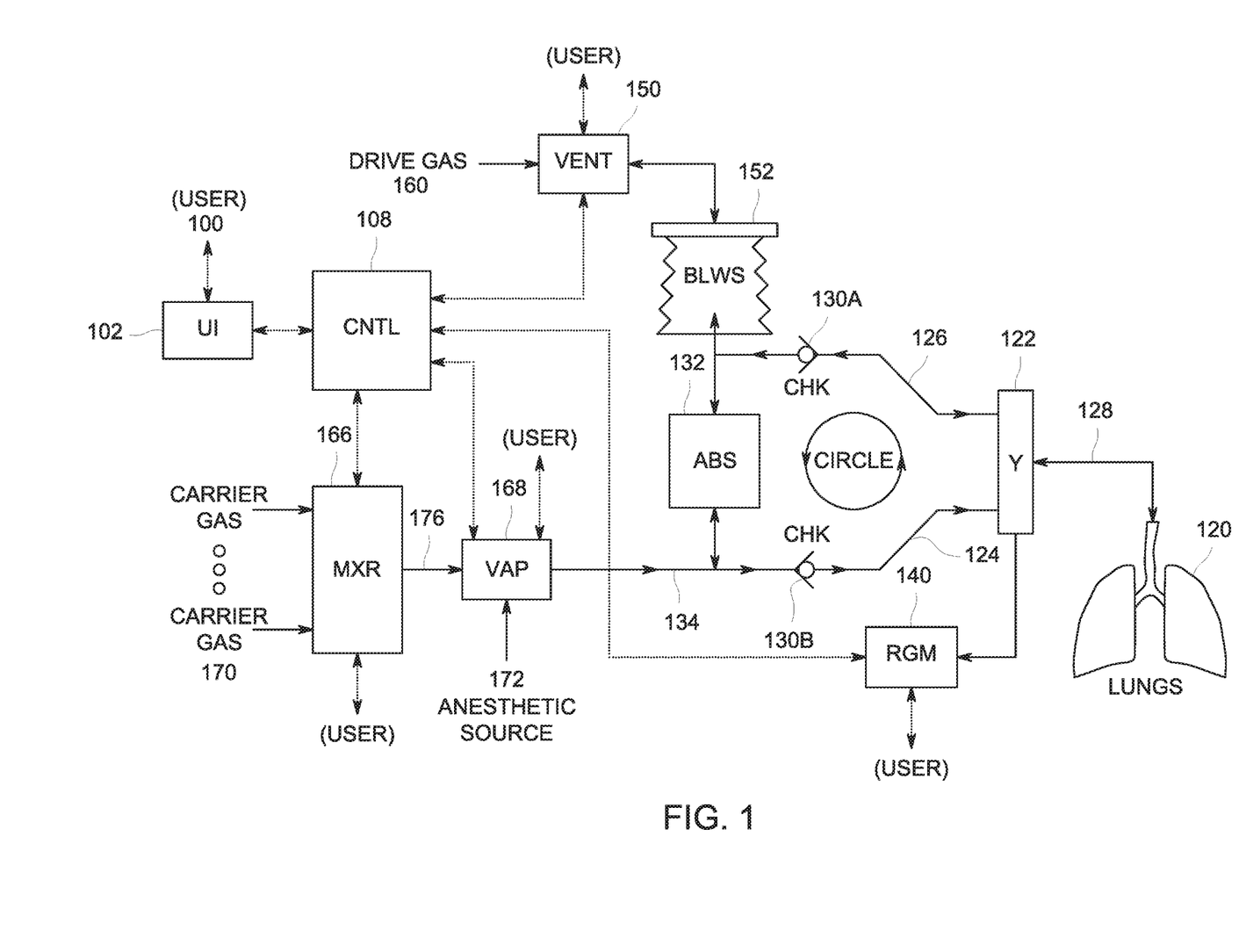
FIG. 1 depicts a general topology of an inhaled anesthesia administration, in accordance with aspects of the present disclosure.

With the preceding in mind, and to provide useful context and background, a general topology of an inhaled anesthesia administration is illustrated in FIG. 1. With reference to this figure, a clinician, or user 100, interacts with a user interface 102 or various subsystems to direct an anesthesia machine to ventilate a patient's lungs 120 with an appropriate breathing gas mix. The user interface 102 or various subsystems provide for the acceptance of input from, and the provision of output to, the user 100. The user interface 102 communicates with a system controller 108, which directs or coordinates the various subsystems. At a low level, the depicted subsystems act on the gases in response to the commands received from the user 100 via the controller 108 and/or measure parameters and pass them to the user 100 or to the controller 108 for processing and/or display.

As shown in FIG. 1, the patient and the target lungs 120 are connected to the machine with a patient breathing circuit configured in a Y arrangement 122. Gas flow coming from, and returning to, the machine travels in separate respective legs of the Y, while flow from/to the patient travels in the common leg 128 of the Y. On the machine side, gas to the patient flows in an inspiratory limb 124, and gas returning from the patient travels in an expiratory limb 126. Gas is directed to the appropriate limb through the action of flow check valves 130 placed in each. Often, the limbs are connected through an absorber 132, which routes the gas from the expiratory limb 126 back to the inspiratory limb 124, while passing the gas through a material to remove the exhaled carbon dioxide from the patient. This arrangement is known as a circle system, with recirculating gas flow as indicated. In some implementations, a respiratory gas monitor (RGM) 140 may be present to sample gas inspired and expired by the patient. Such an RGM 140 may be positioned in the patient breathing circuit for the purpose of measuring gas parameters and reporting them to the user interface 102 or possibly directly by the monitor. As discussed herein, in certain implementations, such an RGM 140 may be absent or certain functionality may be dedicated to the vaporizer 168 (discussed below) instead.

Often during the practice of anesthesia mechanical assistance is used to drive breathing gases into and receive gas out of the patient's lungs 120, thus facilitating recirculation. For example, in the depicted implementation, the ventilator 150 coordinates operation of a gas bellows 152 to deliver gas during inspiration and to receive gas during expiration. During inspiration, the ventilator 150 contracts the bellows 152, closing the check valve 130A in the expiratory limb 126 and opening the check valve 130B in the inspiratory limb 124. Gas in the bellows 152 then flows through the absorber 132 and down the inspiratory limb 124 to the patient. During expiration, the ventilator 150 allows the bellows 152 to expand, closing the check valve 130B in the inspiratory limb 124 and opening the check valve 130A in the expiratory limb 126. The bellows 152 then fills with gas from the patient in addition to upstream replenishment gas from the fresh gas limb 134. The ventilator 150 drives the bellows 152 in response to communication with the user 100 or controller 108, often using a pressured drive gas source 160.

As gas is consumed by the patient via uptake in the lungs 120, it is replaced. This is accomplished by the action of the medical gas mixer 166 and medical vaporizer 168. The gas mixer 166 may be connected to a number of gas sources 170 at its inputs, and acts to select and mix these gases to create a carrier gas 176 having a gas flow and a component gas concentration consistent with communications with the user 100 or controller 108. In some implementations, the carrier gas 176 may be or may include a conventional respiratory gas or blend of gases, such as oxygen, nitrous oxide, or air, or other suitable carrier gases, such as carbon dioxide or heliox. The output of the gas mixer 166 is connected to the input of the vaporizer 168 such that the gas from the mixer 166 becomes the carrier gas for the anesthetic gas produced by the vaporizer 168. An anesthetic source 172 is input to the vaporizer 168, which serves to convert the anesthetic to gas form if needed and mix it with the carrier gas 176 to a concentration consistent with communications with the user 100 or the controller 108. Examples of suitable anesthetics include, but are not limited to, desflurane, enflurane, halothane, isoflurane, sevoflurane, xenon, and so forth. The output of the vaporizer 168 is connected to the fresh gas limb 134.

With the preceding general overview in mind, aspects of the present approach related to the operation of the vaporizer 168 are described.

Conventional medical vaporizers may address concentration output accuracy in the face of unknown and/or varying input carrier gas composition in a variety of ways, especially with regards to nitrous oxide levels present. Stand-alone vaporizers, intended to operate with any possible input carrier gas from the host anesthesia machine, typically stay within standards but with significantly degraded output accuracy. Integrated vaporizers, which are configured to receive information defining the composition of the input carrier gas coming from the host, typically cannot operate and shut down if the information is lost. Planned vaporizers, which use a relative sensing scheme to reduce the effects, typically stay within standards but with moderately degraded output accuracy. Thus, for known medical vaporizers, operation is not possible or output concentration accuracy is at least moderately degraded with unknown and/or varying input carrier gas composition.

Figure 2:
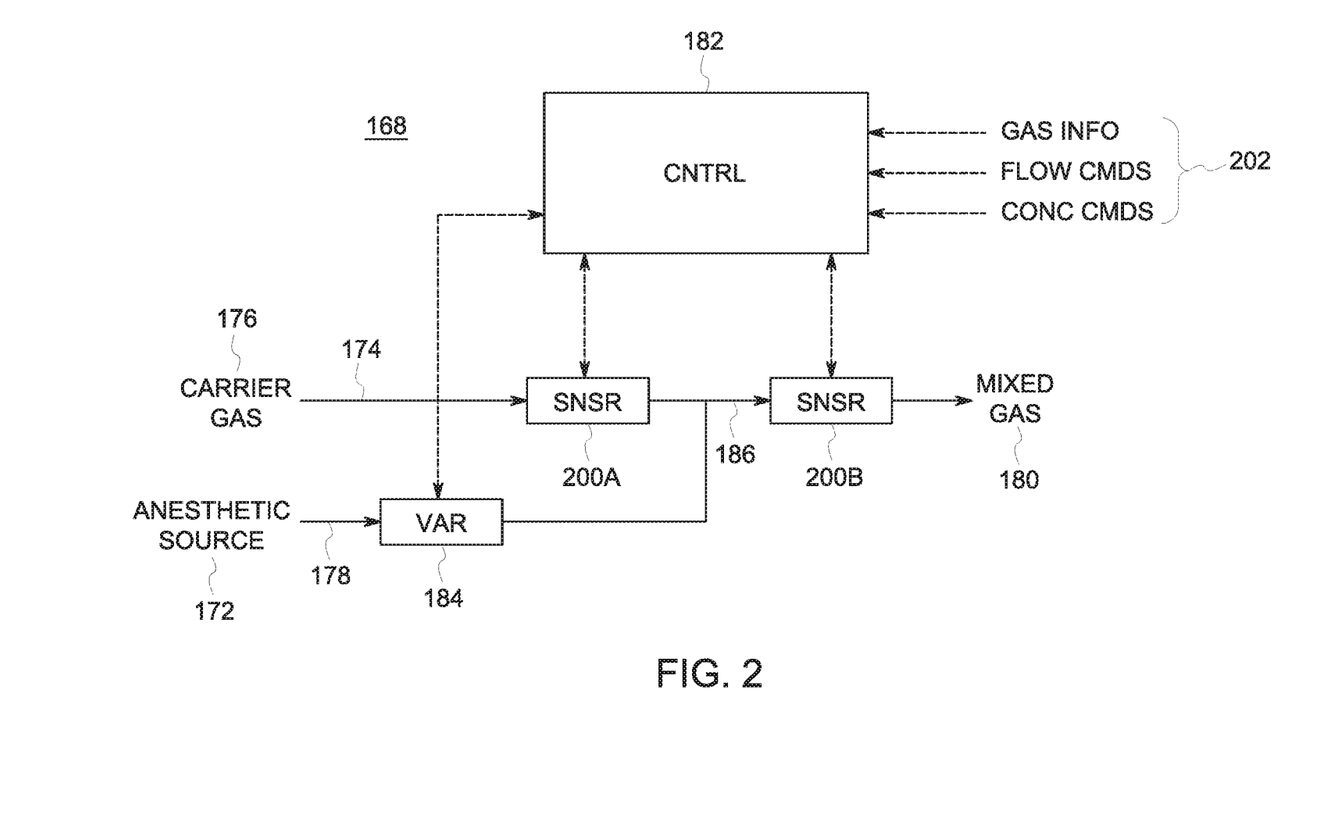
FIG. 2 depicts a topology of a vaporizer, in accordance with aspects of the present disclosure.

A medical vaporizer topology in accordance with the present approach is shown in FIG. 2. In the depicted example, an input carrier gas 176 from the host anesthesia machine is received via a respective input and is blended with an anesthetic agent 172, to generate a blended or mixed gas 180 that is output via a mixed gas channel 186. The carrier gas 176, flowing in a main gas channel 174, may in certain embodiments be unknown (i.e., of unknown identity and/or properties) and possibly of varying composition. The anesthetic agent 172, flowing in a side gas channel 178, is known by the vaporizer controller 182 as a pre-configured input or based on information received during real time operation. The vaporizer controller 182 uses this information, along with a flow ratio and/or concentration command from the user 100 or system controller 108, to determine the current vaporizer 168 operating state and compute the internal action required to achieve its desired operating state, consistent with received commands.

In operation, the vaporizer controller 182 changes the drive to a variable valve 184 to achieve a specified flow ratio and/or concentration in response to measurements from separate dual-purpose sensors 200 positioned, respectively in the main gas channel 174 (i.e., in the carrier gas 174) and mixed gas channel 186 (i.e. in the mixed gas 180). The sensor 200A in the main gas channel 174 and the sensor 200B in the mixed gas channel 186 may be dual-purpose sensors, capable of measuring both gas flow and/or concentration.

For the purposes of control, the vaporizer controller 182 computes targets for the flow and/or concentration measurements from its internal sensors 200 based on the flow and/or gas concentration commands 202 it receives from the user 100 or system controller 108. These targets may be in high-level terms, such as gas flow or gas concentration, or they may be in other intermediate or low-level terms, depending on the scheme chosen.

The target flows and/or concentrations may be achieved using a feedback control scheme, where the vaporizer controller 182 operates the variable valve(s) 184 to minimize the difference or error between the target and measured sensor values. An example for concentration is shown below (Equation (1)), where the feedback error for the concentration of a component of the gas in the mixed channel ($e_{cX}$) is formed from the target for the concentration of that component in the mixed channel ($c_{TX}$) and the measured concentration of that mixed gas component in the mixed channel ($c_{MX}$):

$$e_{cX} = c_{TX} - c_{MX} \qquad (1)$$

Other effective feedback error terms and controls schemes are also possible, (depending on the choices made for combination of targets and measurements, and error comparison), and the present examples are provided solely to provide context and to facilitate explanation.

As discussed herein, the present vaporizer topology incorporates dual-purpose sensors, each capable of concurrently measuring two parameters of a monitored gas, such as both gas flow and gas concentration. These measurements may be used for control, safety, computation and/or reporting of other clinically useful information, and so forth. One example of such a dual-purpose sensor is an ultrasonic sensor, as discussed herein, and the present examples and discussion are presented in the context of such an ultrasonic sensor. It should be appreciated, however, that such examples are provided only for the purpose of explanation and to provide a useful, real world context and that other suitable sensors are also encompassed by the present discussion.

With respect to ultrasonic sensors, such sensors operate based on principles related to sound propagation. With respect to these underlying concepts, sound (which may be understood to be the propagation of acoustic waves in a medium) is influenced by both gas flow and gas composition, the latter being directly related to individual gas component concentration. In particular, the longitudinal speed of propagation of the acoustic waves, i.e., the speed-of-sound, is influenced by both flow and concentration of the medium through which the waves propagate.

A simple physics model (Equation (2)) of the speed-of-sound (v) in a gas flowing at flow rate (F) is shown below, having two terms, one ($v_m$) related to the flow rate, and the other ($v_s$) related to the gas medium's properties. The effect of gas flow may increase or decrease the overall speed-of-sound and is modulated by inclination angle ($\alpha$) depending on the direction of sound relative to the direction of gas flow.

$$v = v_s \pm v_m \sin \alpha \qquad (2)$$

The first term ($v_s$) depends on heat capacity ratio ($\gamma$) and molar mass (M), having values which are characteristic of each gas, as well as gas temperature (T) as shown in Equation (3) below. Also included is the molar gas constant (R).

$$v_s = \sqrt{\frac{\gamma RT}{M}} \qquad (3)$$

Properties of mixed gases can be related back to those of the component gases ($\gamma_1$, $M_1$, $\gamma_2$, $M_2$) as shown in Equations (4, 5) below and through the gas concentration (c) of either component.

$$\gamma = 1 + \left( \frac{c}{\gamma_1 - 1} + \frac{1-c}{\gamma_2 - 1} \right)^{-1} \qquad (4)$$

$$M = cM_1 + (1-c)M_2 \qquad (5)$$

The second term ($v_m$) depends on the flow rate and the cross-sectional area (A) of the gas conduit as shown below.

$$v_m = \frac{F}{A} \quad (6)$$

Time-of-flight (t) may be measured using ultrasonic transducers and appropriate electronics and software. Speed-of-sound can be related to the sound path length (d) as shown below.

$$v = \frac{d}{t} \quad (7)$$

Figure 3:
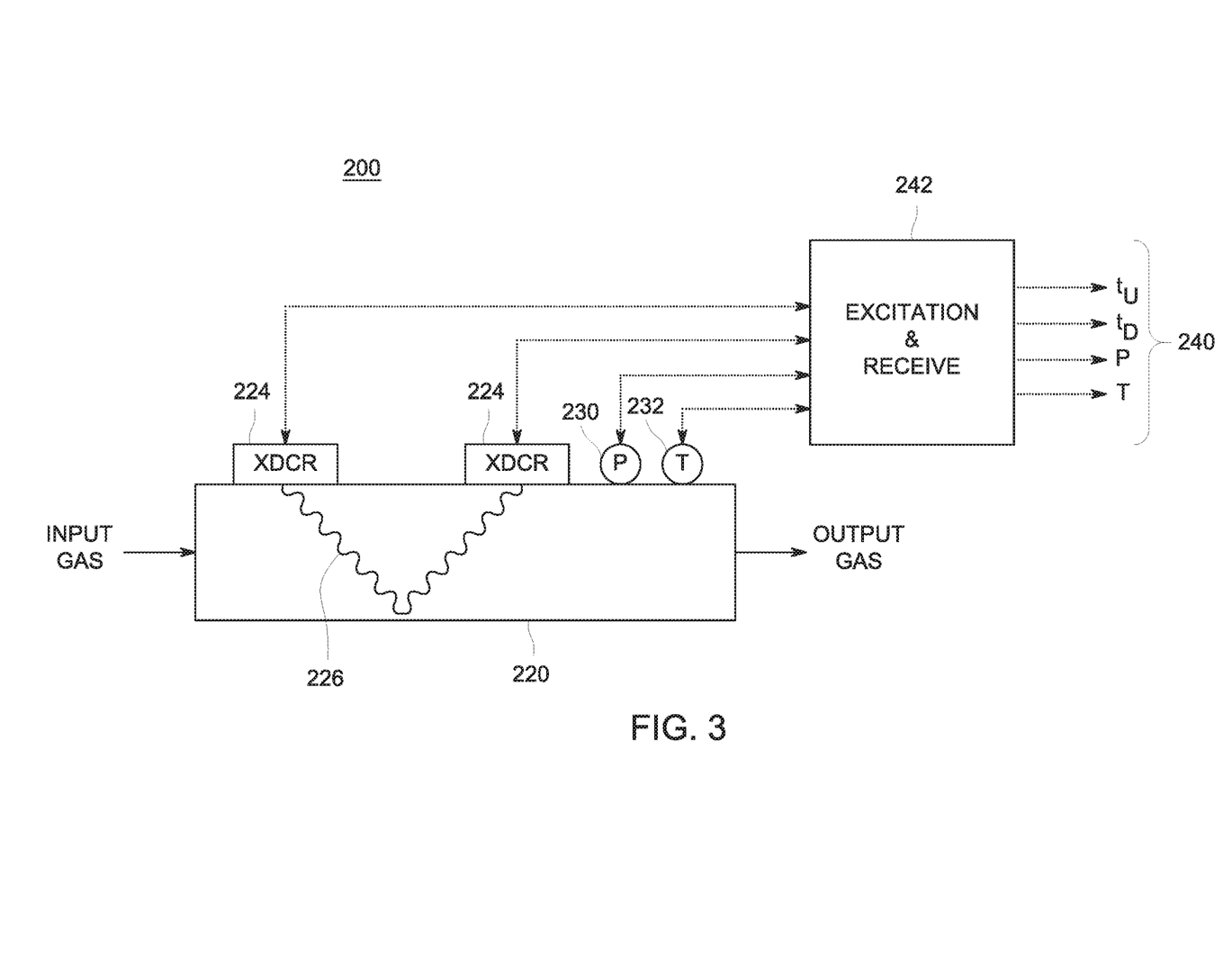
FIG. 3 depicts a schematic of a dual-purpose sensor, in accordance with aspects of the present disclosure.
Figure 4:
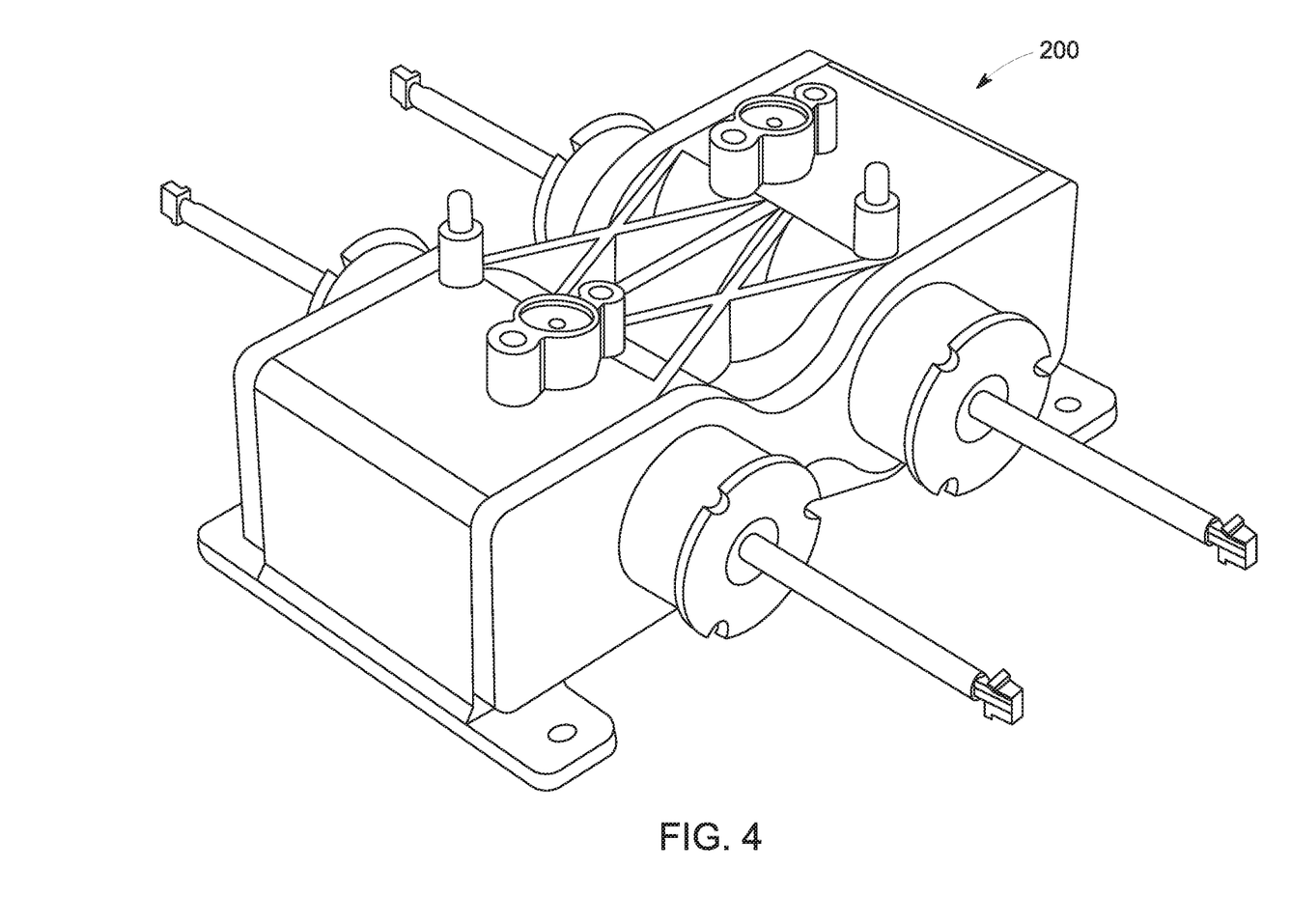
FIG. 4 depicts a perspective view of a physical implementation of a dual-purpose sensor, in accordance with aspects of the present disclosure.

With the preceding in mind, FIG. 3 depicts an example of a dual-purpose sensor in the form of an ultrasonic sensor 200. For reference, a perspective external depiction of a physical embodiment of two adjacently-packaged sensors 200 is provided in FIG. 4. In the depicted example, each ultrasonic sensor 200 includes a gas conduit 220 with an input and output, upon which at least a pair of ultrasonic transducers 224 are positioned such that sound 226 traveling between the transducers 224 is influenced by the gas flow and gas composition in the conduit 220. A temperature transducer 232 and/or pressure transducer 230 may, in certain embodiments, be included to sense the local environmental conditions of the gas in the conduit 220. Depending on the implementation, the transducers 224, 230, 232 may be placed in any number of locations and/or orientations to be effective.

The transducers 224, 230, 232 may be operated by one of (or a combination of) software executed on a suitable microprocessor and/or an application specific integrated circuit (ASIC). Such electrical components may be located within or proximate the sensor 200 or remote from, but in communication with, the sensor 200, such as in a controller (e.g., vaporizer controller 182) or control interface. By way of example such electronics and/or software (illustrated generally as excitation and receive circuitry 242) may, when in operation, generate electrical signals to excite (or otherwise activate or operate) the transducers 224, 230, 232 and/or receive or readout corresponding or responsive electrical signals generated by the transducers 224, 230, 232. The signals acquired from the transducers 224, 230, 232 may be processed into a measurement set 240 for use by the vaporizer controller 182. In one embodiment, the measurement set 240 includes an upstream time-of-flight ($t_U$) and a downstream time-of-flight ($t_D$), in addition to possibly any one or more of a temperature (T) or a pressure (P), as shown by Equation (8). In certain embodiments, an across time-of-flight (which is not affected by flow) may be acquired in addition to or instead of the upstream time-of-flight or downstream time-of-flight as part of the calibration measurement set $$M = \{t_U, t_D, T, P\} \quad (8)$$

The aforementioned time-of-flight measurements may be used to calculate measurements of the flow and/or concentration of the gas in the sensor 200. In some embodiments, one or more of temperature and pressure measurements may also be employed in the gas flow and/or concentration calculations though, as noted above, temperature and pressure measurements are not required.

In the following discussion, "f( )" denotes "is a function of". Measurements having an associated "M" subscript relate to the main gas channel 174, while those with an associated "X" subscript relate to the mixed gas channel 186. As discussed below, gas flow may be calculated using upstream and downstream time-of-flight alone or, in certain embodiments, may incorporate some or all of the other measurements that may be present in a given sensor's measurement set 240. Thus, main gas flow (Equation (9)) and mixed gas flow (Equation (10)) may be given as:

$$F_M = f(t_{UM}, t_{DM}, T_M, P_M) \quad (9)$$

$$F_X = f(t_{UX}, t_{DX}, T_X, P_X) \quad (10)$$

The time-of-flight measurements, either alone or in combination with temperature and/or pressure measurements, may also be used to calculate a measurement of the concentration (Equations (11, 12)) of the component gases in the respective conduits 220. In particular, the concentration of component gases in one or both of the main gas channel 174 or mixed gas channel 186 as a function of the time-of-flight measurements noted herein may be calculated. For the main gas channel 174, this is accomplished using at least one of the upstream or downstream time-of-flight measurements from sensor 200A. For the mixed gas channel 186, this is accomplished using at least one of the upstream or downstream time-of-flight measurements from each sensor 200. Other possible combinations of time-of-flight measurements are also effective for this calculation. In addition, temperature measurements (if available) may also be employed in the gas concentration calculation, as shown below. As noted above, however, temperature measurements are not necessary for the calculation. Thus, a main gas component concentration (Equation (11)) and mixed gas component concentration (Equation (12)) may be given as:

$$c_M = f(t_{UM}, T_m) \quad (11)$$

$$c_X = f(t_{UM}, t_{UX}, T_M, T_X) \quad (12)$$

With the preceding discussion of ultrasonic sensors 200 in mind, additional detail of an implementation of the vaporizer topology of FIG. 2 when using ultrasonic sensors 200 may be provided. With respect to the following discussion, measurements taken during and/or resulting from a calculation following calibration are denoted using a bar ( ) over the corresponding symbol.

With this in mind, during calibration the ultrasonic sensor 200A in the main channel is exposed to a known gas with known properties, and a calibration measurement set is taken. This calibration measurement set ($\overline{M}$) includes one of more of an upstream time-of-flight and a downstream time-of-flight, and may or may not include a temperature measurement and/or a pressure measurement, as shown in Equation (13).

$$\overline{M} = \{\overline{t_U}, \overline{t_D}, \overline{T}, \overline{P}\} \quad (13)$$

In one implementation, the calibration measurement set $\overline{M}$ is stored in a non-volatile manner, such as within a non-volatile storage medium of the ultrasonic sensor 200 and/or the vaporizer controller 182.

During real time operation (e.g., clinical use), the ultrasonic sensor 200A in the main channel 174 is exposed to an unknown gas with possibly varying composition (carrier gas 176), and measurement sets (M) are repeatedly provided by the ultrasonic sensor 200A. The identity ($I_M$) and/or concentration ($c_M$) of one or more components of the gas in the input carrier gas 176 is computed by the vaporizer controller 182 using the calibration measurement set $\overline{M}$ and real time measurement sets (M). This is accomplished, in one implementation, using at least one of the upstream or downstream time-of-flight measurements from the calibration and real time measurement sets. In some instances, these determinations may also utilize one or more of the available temperature measurements, as shown in Equation (14) and Equation (15). Note there are other possible combinations of time-of-flight measurements that are also effective for these calculations.

$$I_M = f(t_U, \overline{t_U}, T, \overline{T}) \quad (14)$$

$$c_M = f(t_U, \overline{t_U}, T, \overline{T}) \quad (15)$$

Once the identity and/or concentration of one or more components of the input carrier gas 176 is known, this information may be provided to a user 100, such as via an output visual display device and/or may be utilized by one or more control or monitoring operations of the vaporizer 168. The output visual display device may conveniently display one or more of concentration of components of the mixed gas 180 output by the vaporizer 168 or one or more of the identity or concentration of one or more of the components of the input carrier gas 176.

Within the vaporizer 168, the identity and/or concentration of one or more components of the gas in the main gas channel 174 can be used to correct computed measurements of flow in the main and/or mixed channels 174, 186 as well as the computed concentrations in the mixed gas channel 186. The corrections improve the accuracy of flow and/or concentration measurements, the latter leading to improved vaporizer output concentration accuracy.

With respect to the following discussion, calculated measurements after correction are denoted using a hat (^) over the corresponding symbol. Corrected flow measurements ($\hat{F}$) (Equations (16), (17)) and concentration measurements ($\hat{c}$) (Equation (18)) may be calculated as shown below, using a flow correction factor for the main and mixed channels ($A_{FM}$, $A_{FX}$) and a concentration correction factor ($A_{cX}$) for a component gas concentration in the mixed channel. Once calculated, the corrected flows and/or the corrected concentrations may be displayed or used in subsequent calculations, such as for modifying control or monitoring operations of the medical vaporizer 168. Note there may be other possible correction factors that may also be applied.

$$\hat{F}_M = A_{FM} F_M \quad (16)$$

$$\hat{F}_X = A_{FX} F_X \quad (17)$$

$$\hat{c}_X = A_{cX} c_X \quad (18)$$

The correction factors may be based on an understanding of the underlying physics behind how a particular possible unknown gas and/or composition appearing in the input carrier gas 176 affects the calculated measurements of flow in the main and mixed channels 174, 186 and concentrations in the mixed channel 186, or they may be empirically developed. The correction factor for flow in the main channel 186 may depend on the determined identity and/or concentration of a component gas in the main channel 174. By way of example, certain of the measurements shown in Equation (19) may be relevant to determining a main channel flow correction factor:

$$A_{FM} = f(I_M, c_M, F_M, T_M, P_M) \quad (19)$$

Similarly, the correction factor for flow in the mixed channel 186 may depend on the determined identity and/or concentration of a component gas in the main channel 174. By way of example, certain of the measurements shown in Equation (20) may be relevant to determining a mixed channel flow correction factor:

$$A_{FX} = f(I_M, c_M, F_X, T_X, P_X, c_X) \quad (20)$$

The correction factor for concentration of a component gas in the mixed channel 186 may depend on the determined identity and/or concentration of a component gas in the main channel 174. By way of example, certain of the measurements shown in Equation (20) may be relevant to determining a mixed channel concentration correction factor:

$$A_{cX} = f(I_M, c_M, c_X, T_X) \quad (20)$$

Technical effects of the invention include providing a medical vaporizer design that is able to measure and report the total anesthetic being delivered at the vaporizer output, including that coming from the medical gas mixer and vaporizer itself. This approach can also facilitate the capability for the vaporizer to self-correct its output and any reported parameters when the input carrier gas is unknown and/or of variable composition. At the same time, medical vaporizer cost can be minimized.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical vaporizer, comprising:
a main gas channel through which a first gas flows during operation, wherein the first gas is unknown to a vaporizer controller;
a side gas channel, comprising one or more side channel control valves that during operation control a second flow of a second gas through the side gas channel;
a mixed gas channel configured to receive the first flow of the first gas and the second flow of the second gas during operation and to output a mixed gas;
a first dual-purpose sensor positioned in the main gas channel and configured to generate a first set of measurements during operation;
a second dual-purpose sensor positioned in the mixed gas channel and configured to generate a second set of measurements during operation, wherein the first and second dual-purpose sensors are each configured both to measure gas flow and generate measurements for gas concentration; and
the vaporizer controller configured to receive the first set of measurements, the second set of measurements, and a stored calibration measurement set, to calculate one or more of the identity of one or more components of the first gas or concentration of one or more components of the first gas based on the first set of measurements and the stored calibration measurement set, to calculate concentration of one or more components of the mixed gas based on the second set of measurements, and to control operation of one or more of the side channel control valves based upon one or more of the calculated identities or concentrations, wherein the stored calibration measurement set is derived from time-of-flight measurements by the first dual-purpose sensor of a known gas flowing through the main gas channel, and wherein the vaporizer controller is configured to utilize the calculated identity or concentration of the one or more components of the first gas flowing in the main gas channel to correct measurements of gas flow in one or more of the main gas channel and the mixed gas channel and to correct the calculated concentration of the one or more components of the mixed gas in the mixed gas channel.

2. The medical vaporizer of claim 1, wherein the vaporizer controller is further configured to display one or more of the identity of one or more components of the first gas, concentration of one or more components of the first gas, or concentration of one or more components of the mixed gas.

3. The medical vaporizer of claim 1, wherein no dual-purpose sensor is positioned in the side gas channel.

4. The medical vaporizer of claim 1, wherein at least one of the first set of measurements or the second set of measurements comprises one or more time-of-flight measurements.

5. The medical vaporizer of claim 1, wherein the first dual-purpose sensor and the second dual-purpose sensor comprise ultrasonic sensors.

6. The medical vaporizer of claim 5, wherein the ultrasonic sensors each comprise a pair of ultrasonic transducers.

7. The medical vaporizer of claim 5, wherein the ultrasonic sensors further comprise one or both of a pressure transducer or a temperature transducer.

8. The medical vaporizer of claim 1, wherein one or both of the identity or properties of the first gas are unknown to the vaporizer controller.

9. The medical vaporizer of claim 1, wherein one or both of the first gas or second gas may be a pure gas or a gas blend.

10. The medical vaporizer of claim 1, wherein the vaporizer controller is configured to utilize the calculated identity or concentration of the one or more components of the first gas flowing in the main gas channel to determine one or more flow correction factors for correcting the measurements of gas flow in one or more of the main gas channel and the mixed gas channel and to determine a concentration correct factor for correcting the calculated concentration of the one or more components of the mixed gas in the mixed gas channel.

* * * * *